(12) United States Patent
Sapir et al.

(10) Patent No.: US 7,599,893 B2
(45) Date of Patent: Oct. 6, 2009

(54) METHODS AND SYSTEMS FOR FEATURE SELECTION IN MACHINE LEARNING BASED ON FEATURE CONTRIBUTION AND MODEL FITNESS

(75) Inventors: Marina Sapir, Mamaroneck, NY (US); Faisal M. Khan, New Rochelle, NY (US); David A. Verbel, New York, NY (US); Olivier Saidi, Greenwich, CT (US)

(73) Assignee: Aureon Laboratories, Inc., Yonkers, NY (US)

( * ) Notice: Subject to any disclaimer, the term of this patent is extended or adjusted under 35 U.S.C. 154(b) by 155 days.

(21) Appl. No.: 11/438,789

(22) Filed: May 22, 2006

(65) Prior Publication Data

US 2007/0112716 A1 May 17, 2007

Related U.S. Application Data

(60) Provisional application No. 60/726,809, filed on Oct. 13, 2005.

(51) Int. Cl.
*G06F 15/18* (2006.01)

(52) U.S. Cl. .............................. 706/12; 706/14; 706/20; 706/47; 382/128; 382/129; 382/133; 382/134; 600/300; 600/301

(58) Field of Classification Search .................. 706/12, 706/14, 17–21, 47, 52; 382/128–134; 600/300, 600/301
See application file for complete search history.

(56) References Cited

U.S. PATENT DOCUMENTS

| 5,649,068 | A | * | 7/1997 | Boser et al. .................... 706/12 |
| 5,890,143 | A | * | 3/1999 | Sakurai ........................ 706/12 |
| 6,910,192 | B2 | * | 6/2005 | McConaghy .................... 716/2 |
| 6,995,020 | B2 | | 2/2006 | Capodieci et al. |
| 7,321,881 | B2 | | 1/2008 | Saidi et al. |
| 7,326,575 | B2 | | 2/2008 | Capodieci et al. |
| 7,389,277 | B2 | * | 6/2008 | Chen et al. ..................... 706/21 |
| 7,461,048 | B2 | | 12/2008 | Teverovskiy et al. |
| 7,467,119 | B2 | | 12/2008 | Saidi et al. |
| 7,483,554 | B2 | | 1/2009 | Kotsianti et al. |
| 7,505,948 | B2 | | 3/2009 | Saidi et al. |
| 2003/0004402 | A1 | * | 1/2003 | Hitt et al. ...................... 600/300 |
| 2003/0018595 | A1 | * | 1/2003 | Chen et al. ..................... 706/12 |
| 2004/0015337 | A1 | * | 1/2004 | Thomas et al. ................. 703/11 |
| 2005/0043593 | A9 | * | 2/2005 | Hitt et al. ...................... 600/300 |
| 2005/0131847 | A1 | * | 6/2005 | Weston et al. .................. 706/12 |
| 2005/0267850 | A1 | * | 12/2005 | Chen et al. ..................... 706/12 |
| 2006/0047611 | A1 | * | 3/2006 | Selifonov et al. .............. 706/13 |
| 2006/0064248 | A1 | | 3/2006 | Saidi et al. |
| 2006/0199213 | A1 | | 9/2006 | Capodieci et al. |
| 2007/0154958 | A1 | | 7/2007 | Hamann et al. |

OTHER PUBLICATIONS

Guyon, "Gene Selection for Cancer Classification Using Support Vector Machines," *Machine Learning*, 46, pp. 389-422, 2002.

* cited by examiner

*Primary Examiner*—David R Vincent
*Assistant Examiner*—Omar F Fernandez Rivas
(74) *Attorney, Agent, or Firm*—Mintz, Levin, Cohn, Ferris, Glovsky & Popeo, P.C.

(57) ABSTRACT

Methods and systems are provided for feature selection in machine learning, in which the features selected for inclusion in a prediction rule are selected based on statistical metric(s) of feature contribution and/or model fitness.

26 Claims, 5 Drawing Sheets

Experiment 1:

| Sub-experiment, Cohort, Features | Without Feature Selection Procedure 100 (FIG. 1) | | With Feature Selection Procedure 100 (FIG. 1) | |
|---|---|---|---|---|
| Sub-experiment 1, Cohort 1, Clinical+AR | Training CI: | 0.86 | Training CI: | 0.86 |
| | Training Sensitivity: | 0.82 | Training Sensitivity: | 0.82 |
| | Training Specificity: | 0.78 | Training Specificity: | 0.8 |
| | Training Fitness: | 1.5 | Training Fitness: | 1.52 |
| | Validation CI: | 0.76 | Validation CI: | 0.75 |
| | Validation Sensitivity: | 0.79 | Validation Sensitivity: | 0.79 |
| | Validation Specificity: | 0.61 | Validation Specificity: | 0.61 |
| | Validation Fitness: | 1.24 | Validation Fitness: | 1.23 |
| | Number of Features | 10 | Number of Features | 6 |
| Sub-experiment 2, Cohort 1, Clinical+AR+Imaging v5.0 | Training CI: | 0.82 | Training CI: | 0.83 |
| | Training Sensitivity: | 0.79 | Training Sensitivity: | 0.82 |
| | Training Specificity: | 0.81 | Training Specificity: | 0.81 |
| | Training Fitness: | 1.46 | Training Fitness: | 1.49 |
| | Validation CI: | 0.81 | Validation CI: | 0.8 |
| | Validation Sensitivity: | 0.91 | Validation Sensitivity: | 0.91 |
| | Validation Specificity: | 0.7 | Validation Specificity: | 0.7 |
| | Validation Fitness: | 1.45 | Validation Fitness: | 1.43 |
| | Number of Features | 43 | Number of Features | 6 |
| Sub-experiment 3, Cohort 1, Clinical+AR+Nucleic Density Imaging | Training CI: | 0.87 | Training CI: | 0.87 |
| | Training Sensitivity: | 0.79 | Training Sensitivity: | 0.79 |
| | Training Specificity: | 0.84 | Training Specificity: | 0.85 |
| | Training Fitness: | 1.54 | Training Fitness: | 1.54 |
| | Validation CI: | 0.8 | Validation CI: | 0.8 |
| | Validation Sensitivity: | 0.85 | Validation Sensitivity: | 0.85 |
| | Validation Specificity: | 0.73 | Validation Specificity: | 0.73 |
| | Validation Fitness: | 1.42 | Validation Fitness: | 1.41 |
| | Number of Features | 14 | Number of Features | 10 |

FIG. 3

Experiment 2:

| Sub-experiment, Cohort, Features | Without Feature Selection Procedure 100 (FIG. 1) | | With Feature Selection Procedure 100 (FIG. 1) | |
|---|---|---|---|---|
| Sub-experiment 1, Cohort 1+2, Clinical+AR | Training CI: | 0.84 | Training CI: | 0.84 |
| | Training Sensitivity: | 0.79 | Training Sensitivity: | 0.81 |
| | Training Specificity: | 0.75 | Training Specificity: | 0.74 |
| | Training Fitness: | 1.43 | Training Fitness: | 1.43 |
| | Validation CI: | 0.75 | Validation CI: | 0.75 |
| | Validation Sensitivity: | 0.79 | Validation Sensitivity: | 0.79 |
| | Validation Specificity: | 0.61 | Validation Specificity: | 0.61 |
| | Validation Fitness: | 1.23 | Validation Fitness: | 1.23 |
| | Number of Features | 10 | Number of Features | 6 |
| Sub-experiment 2, Cohort 1+2, Clinical+AR+Imaging v5.0 | Training CI: | 0.8 | Training CI: | 0.82 |
| | Training Sensitivity: | 0.74 | Training Sensitivity: | 0.77 |
| | Training Specificity: | 0.83 | Training Specificity: | 0.82 |
| | Training Fitness: | 1.41 | Training Fitness: | 1.45 |
| | Validation CI: | 0.81 | Validation CI: | 0.81 |
| | Validation Sensitivity: | 0.88 | Validation Sensitivity: | 0.85 |
| | Validation Specificity: | 0.67 | Validation Specificity: | 0.67 |
| | Validation Fitness: | 1.4 | Validation Fitness: | 1.38 |
| | Number of Features | 43 | Number of Features | 13 |
| Sub-experiment 3, Cohort 1+2, Clinical+AR+Nucleic Density Imaging | Training CI: | 0.85 | Training CI: | 0.85 |
| | Training Sensitivity: | 0.77 | Training Sensitivity: | 0.84 |
| | Training Specificity: | 0.81 | Training Specificity: | 0.76 |
| | Training Fitness: | 1.47 | Training Fitness: | 1.49 |
| | Validation CI: | 0.8 | Validation CI: | 0.81 |
| | Validation Sensitivity: | 0.82 | Validation Sensitivity: | 0.91 |
| | Validation Specificity: | 0.67 | Validation Specificity: | 0.61 |
| | Validation Fitness: | 1.34 | Validation Fitness: | 1.36 |
| | Number of Features | 14 | Number of Features | 8 |

FIG. 4

| Feature | Weight | Contribution |
|---|---|---|
| bxgg1 | 0.60915 | 0.32711 |
| Bxggtot | -2.9376 | -1.5625 |
| Prepsa | -0.95412 | -0.47061 |
| Ln | -12.282 | -8.5075 |
| Margins | -8.2817 | -7.2311 |
| Ece | -0.868 | -0.85873 |
| Svi | -5 | -3.9645 |
| gg1 | -0.70685 | -0.49308 |
| ggtot | -2.1379 | -1.4629 |
| Arsi | -5.3672 | -3.8183 |
| RelAreaOfLowNucleiDensity | -1.8361 | -1.2061 |
| RelAreaOfMediumNucleiDensity | 2.7571 | 1.7887 |
| RelAreaOfHighNucleiDensity | -0.26635 | -0.16444 |
| AreaOfNucleiInStromaPx10363 | -6.4417 | -3.0245 |

FIG. 5

METHODS AND SYSTEMS FOR FEATURE SELECTION IN MACHINE LEARNING BASED ON FEATURE CONTRIBUTION AND MODEL FITNESS

CROSS-REFERENCE TO RELATED APPLICATION

This claims the benefit of U.S. Provisional Patent Application No. 60/726,809 filed Oct. 13, 2005, which is hereby incorporated by reference herein in its entirety.

FIELD OF THE INVENTION

Embodiments of the present invention relate to methods and systems for selecting features for a prediction rule based on statistical metric(s) of feature contribution and/or model fitness.

BACKGROUND OF THE INVENTION

Machine learning is a form of artificial intelligence whereby information learned from a computer-assisted analysis of data can be used to generate a prediction rule that describes dependencies in data. The prediction rule can be embodied within a computer-implemented model that performs a specific task. Computer-implemented models can be used in a wide variety of applications such as, for example, search engines (e.g., determining whether search results are primarily informational or commercial in content), stock market analysis (e.g., predicting movements in the prices of stocks), and handwriting and image recognition (e.g., determining whether or not a handwriting sample or image matches another sample or image). As another example, computer-implemented models can be used to diagnose medical conditions (e.g., disease such as cancer), predict the time-to-occurrence (e.g., recurrence) of medical conditions, and/or predict the responses of patients to medical treatments.

A computer-implemented model processes data for one or more input features of an "instance" (e.g., a search result, a stock, a handwriting sample, image, or a medical patient) according to the prediction rule in order to provide an output that represents a given outcome for that instance. A feature is a characteristic of the instance. For example, in the medical context, gender is a clinical feature that can take the values of "male" and "female." An outcome is a prediction or other determination for the instance (e.g., time to disease recurrence) that is produced by the prediction rule based on the input data. With respect to linear prediction rules, the relative importance of a given feature (i.e., the degree to which that feature affects the determination of outcome) is characterized by the numeric "weight" of that feature within the prediction rule. A linear prediction rule can determine an outcome as follows:

$$\text{Outcome} = w_1 * f_1 + w_2 * f_2 + \ldots + w_n * f_n + b \quad (1)$$

where $f_1$ to $f_n$ are measurements for the instance of the n features in the prediction rule, $w_1$ to $w_n$ are the respective weights of the features in the prediction rule, and b is a constant term.

Determining the weights of the features within the linear prediction rule involves applying a machine learning method such as a support vector machine ("SVM") having a linear kernel to data for a cohort of instances (a "training" dataset). The training dataset typically includes measurements of the features for each of the instances, and the known outcomes of those instances. A machine learning tool capable of performing Support Vector Regression for censored data ("SVRc") may be used that can generate the feature weights based on "non-censored" data (i.e., data for instances with known outcomes) and/or "right-censored" data (i.e., data for subjects with outcomes that are at least partially unknown), as is described in commonly-owned U.S. patent application Ser. No. 10/991,240, filed Nov. 17, 2004 (U.S. Pub. No. 20050108753). The predictive ability of the prediction rule can be tested (validated) by applying the prediction rule to one or more instances (e.g., one or more instances from the training cohort or an independent "test cohort"). The outcome(s) predicted by the prediction rule can be compared to at least partially known outcome(s) for the instances through the use of statistical metrics. An example of such a statistical metric is the concordance index (CI). Additional examples of statistical metrics include sensitivity and specificity, which traditionally have been evaluated for prediction rules with binary outcomes.

Various approaches have been provided for selecting the features for inclusion within a prediction rule. Feature selection is not required in order to create a prediction rule (e.g., a rule could be created based on all features believed to be relevant to a specific task), however it may improve the quality of the prediction rule by (for example) determining the features that are the most important predictors for a specific task, eliminating excessive features, and reducing the number of features for which data must be collected for an instance to be evaluated by the prediction rule. In one approach, features can be selected for a prediction rule based on domain expertise only, such as by a physician selecting n features for the rule based solely on that physician's personal knowledge and experience. However, this approach may cause features that do not improve (e.g., or decrease) the predictive ability of the prediction rule 1 to be included in the rule. This approach also may prevent the discovery of new features that may be relevant to the task, because the relevancy of these new features may not be discernable without the aid of statistical evaluation.

In another approach, feature filtering may be used for feature selection, whereby each feature under consideration for potential inclusion in a prediction rule is evaluated independently in order to determine its predictive ability. The features may be ranked according to their predictive abilities and then some fixed number of the "best" features in the rank may be selected for inclusion in the rule.

In other approaches, greedy forward and/or greedy backward procedures can be used alone or in combination with domain expertise to select features for a prediction rule. The greedy forward procedure increases, one feature at a time, the number of features that are considered within a final prediction rule (i.e., the prediction rule resulting from the procedure), where the set of n features eligible for consideration within the prediction rule may be defined based on, for example, domain expertise. However, significant processing resources (e.g., number of processes) are required to implement the greedy forward procedure. Particularly, the first feature selected for inclusion in the final prediction rule according to the greedy forward procedure is the feature that, by itself, forms the one-feature prediction rule that is most predictive of the event under consideration. Thus, in a first stage, the greedy forward procedure involves generating n one-feature prediction rules and then evaluating the predictive abilities of those rules according to a statistical metric such as the CI. The second feature selected for inclusion in the final prediction rule is the feature that, when coupled with the first feature, causes the greatest increase in the predictive ability. This second feature is determined by generating and evaluating the predictive abilities of n−1 two-feature prediction rules (i.e., each rule including the first feature and a respective one of the n−1 features remaining in the set of features eligible for consideration). The third feature selected for inclusion in the final prediction rule is determined by generating and evaluating n−2 three-feature prediction rules, the fourth feature is determined by generating and evaluating n−3 four-feature prediction rules, and so on. This procedure ends when the set of features eligible for inclusion within the final prediction rule lacks any single feature that, when coupled with the currently selected features, would cause an increase in predictive ability. Thus, starting with a set of n features, the greedy forward procedure can require the generation of as many as n+(n*(n−1))/2 prediction rules in order to produce the final prediction rule. For example, starting with a set of 50 features, the greedy forward procedure can require the generation of as many as 50+50*49/2=1275 prediction rules in order to select the features for the final prediction rule. Starting with a set of 500 features, the generation of as many as 500+500*499/2=125,250 prediction rules can be required.

The greedy backward procedure removes features one at a time from a set of features selected for inclusion in a prediction rule, where the features included in the rule at the start of the procedure can be selected based on domain expertise and/or or the greedy forward procedure. Particularly, starting with a prediction rule that includes n features, n(n−1)-feature prediction rules are generated (e.g., by applying SVM or SVRc) and evaluated for their predictive abilities according to a statistical metric such as the CI, with each of the rules leaving out a respective one of the n features. The (n−1)-feature prediction rule, if any, that shows the greatest increase in predictive ability compared to the n-feature prediction rule, or that has the same predictive ability as the n-feature rule when no (n−1)-feature rule has an increased predictive ability, is selected as the new prediction rule. The greedy backward procedure ends when it is determined that the predictive ability of the current prediction rule would decrease with the removal of any single feature. Thus, the greedy backward procedure does not consider that, even when the removal of the first feature causes the predictive ability of a prediction rule to decrease, the predictive ability of the rule could increase overall upon the removal of two or more features.

In view of the foregoing, it would be desirable to provide sound alternatives to the traditional approaches for feature selection in machine learning.

SUMMARY OF THE INVENTION

The above and other objects and advantages of the present invention are provided in accordance with the principles of the present invention, in which (for example) feature(s) are selected for a prediction rule based on statistical metric(s) of feature contribution and/or model fitness. The present invention may be implemented, at least in part, by a computer system.

In an aspect, an apparatus and method are provided for selecting features for a final prediction rule. The final prediction rule produced by the apparatus and method may be embodied as a computer-implemented model (also referred to as a "computer model") that is operative to receive data for one or more features of an instance, process the data according to the prediction rule, and output an outcome as a result of the process. A prediction rule may be generated based on data for a cohort of instances, where initially each instance includes data for n features (e.g., n features selected based on domain expertise) and an outcome to the extent known. For example, the prediction rule may be a linear prediction rule and may be generated by SVRc with a linear kernel. The prediction rule may be evaluated according to a metric of rule fitness in order to produce a fitness value for the rule. The importance of each of the n features may be evaluated according to a metric of feature contribution in order to produce a contribution value for each of the features. A feature may be removed from the set of n features based on the contribution values, for example, by removing the feature that has the lowest absolute value of contribution. Iteratively, this procedure may be repeated in order to produce n prediction rules and n rule fitness values, without regard to whether each iteration produces a prediction rule having a higher, lower, or the same predictive ability as the previous rule. Then, based on the fitness values for the n prediction rules, one of the n rules may be selected as the final prediction rule.

In another aspect, a statistical metric is provided for determining the contribution of a feature to a prediction rule. For example, any of the contribution metrics described below can be used for the given method of feature selection just described. As another example, the contribution metric(s) can be used but for any other filter-type feature selection method.

In an embodiment, the weight of a feature in a linear predictive model can be used as a measure of the feature contribution.

In another embodiment, the variance of a feature can be used as a measure of the feature contribution. For example, the larger the variance, the larger is the ability of the feature to predict outcome.

In yet another embodiment, statistic(s) characterizing the correlation between feature and outcome can be used as a measure of feature contribution. For example, for continuous features and outcomes, the concordance index (CI) or the coefficient of linear correlation can be used. For discrete (nominal) features and discrete outcomes (classification type of problem), one can use chi_squared, or other measures of difference of proportion.

In another embodiment, any monotone function of the above contribution metrics can be used as a contribution metric to take into account different aspects of feature contribution. For example, one can use:

$$\text{Contribution } f_i = w_i * g(\text{variance}_i)$$

where $w_i$ is the weight of feature $f_i$ within the rule and g is a monotone function of $\text{variance}_i$ that measures the discriminative ability of feature $f_i$ as observed in the data used to generate the rule. For example, in one embodiment, $g(\text{variance}_i)$ may be the variance of feature $f_i$. In another embodiment, $g(\text{variance}_i)$ may be the standard deviation of feature $f_i$, which is the square route of the variance of feature $f_i$. Because values for this contribution metric are determined without regard to the prediction error of the prediction rule, this metric can be used to evaluate feature contribution(s) in prediction rules that were generated based on right-censored data. In another example, this metric can be used to evaluate feature contributions in prediction rules that were generated based on non-censored data alone or in combination with right-censored data.

In still another embodiment, the following metric can be used to measure feature contribution:

$$\text{Contribution } f_i = w_i * CI$$

where $w_i$ is the weight of feature $f_i$ in a linear model and CI is the concordance index (an evaluation of the correlation between the feature and the outcome).

In another aspect, a statistical metric is provided for determining the fitness of a prediction rule (e.g., a prediction rule having a continuous output). For example, any of the fitness metrics described below can be used for the given method of feature selection described above or any other wrapper-type feature selection method. As another example, the fitness metric(s) can be used for any type of model selection.

In an embodiment, the concordance index or some other statistic characterizing the correlation between the prediction rule's output and the known outcomes of the training instances can be used as a fitness metric.

In another embodiment, any measure of distance between the predicted outcome value(s) and actual outcome(s) may be used as a fitness metric. For example, one can use the average absolute difference between the predicted and actual target values as a measure of model fitness.

In yet another embodiment, any of the sensitivity, specificity, accuracy, and positive and/or negative predicted values of the prediction rule can be used as a metric of model fitness (e.g., for binary or binarized outcomes).

In another embodiment, any monotone function with one or more of the above statistics can be used as a metric of model fitness. For example, one can use:

Prediction rule fitness=concordance index(CI)+ sensitivity*specificity.

In an embodiment, right censored data is used to evaluate the term sensitivity*specificity.

In still another embodiment, the following risk functional may be used as a metric of model fitness:

Prediction rule fitness=$R(k, L)$= fitness/$(1-\sqrt{(k(\log(L/k)+1)+\log(L)/2)/L})$ where L is number of instances in the dataset, k is a VC-dimension of the set of functions from which the prediction rule is chosen, and fitness is a function that evaluates quality of fit of the prediction rule. For example, if the prediction rule is linear and the features may be considered statistically independent, the VC-dimension k equals the number of features m. If the features are dependent, a scaling coefficient q, $0<q<1$:$k=q*m$, may be used. The proper coefficient q may be found, for example, by a cross-validation procedure.

Other features and advantages of embodiments of the present invention will be apparent from the detailed description, drawings, and claims.

BRIEF DESCRIPTION OF THE DRAWINGS

For a better understanding of the present invention, reference is made to the following description, taken in conjunction with the accompanying drawings, in which like reference characters refer to like parts throughout, and in which:

FIGS. 3 and 4 are tables that compare prediction rules generated according to the feature selection procedure of FIG. 1 with prediction rules generated without the feature selection procedure, which rules are all predictive of time to recurrence of prostate cancer; and FIG. 5 is a table that shows the weights and contribution values of clinical, molecular, and computer-generated morphometric features subsequent to a first iteration of stages 102 and 106 of the procedure of FIG. 1, in connection with sub-experiment 2 of FIG. 3.

DETAILED DESCRIPTION OF THE INVENTION

Embodiments of the present invention relate to methods and systems that select features for a prediction rule based on statistical metric(s) of feature contribution and/or model fitness. The prediction rule may be embodied as a computer-implemented model that is operative to receive data for one or more features of an instance, process the data according to the prediction rule, and output an outcome as a result of the process. The following description focuses primarily on an example in which a linear predictive model is generated through the use of Support Vector Regression for censored data ("SVRc") with a linear kernel. This is because the particular examples discussed in this specification relate to models for predicting time-to-recurrence of prostate cancer, and extensive experimental experience by the present inventors suggests that the linear model is optimal for time-to-recurrence prediction of prostate cancer. Additionally, SVRc allows for the use of censored data and/or non-censored data, which is advantageous because it is generally desirable to incorporate as much data as possible from as many instances as possible when building computer models. In other embodiments, aspects of the present invention can be used in connection with other types of models and/or in connection with models that predict any other medical or non-medical events, whether these models are generated by other machine learning tools or approaches (e.g., neural networks).

Figure 1:
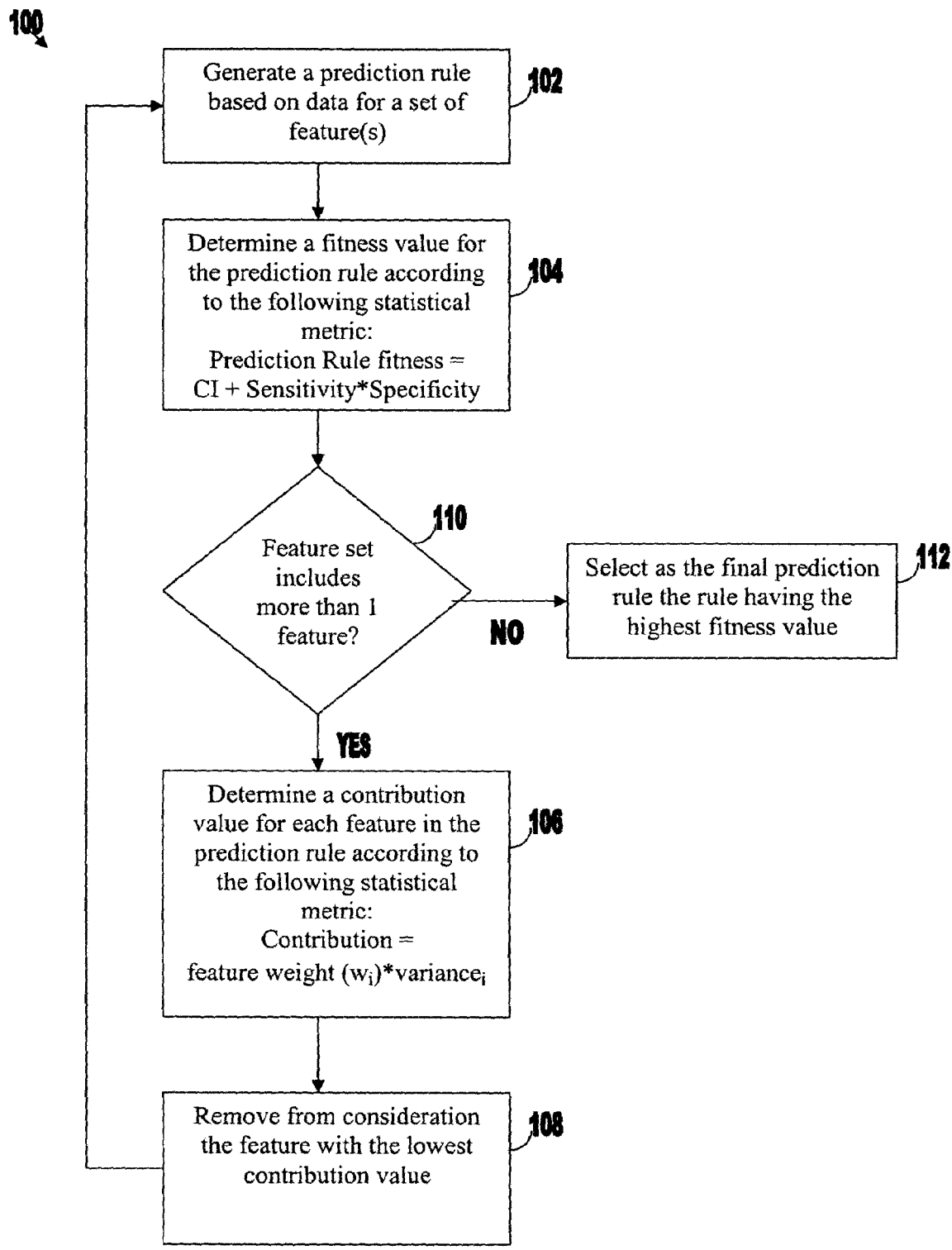
FIG. 1 is a flowchart of illustrative stages involved in selecting features for a prediction rule in accordance with an embodiment of the present invention.

FIG. 1 is a flowchart 100 of illustrative stages involved in selecting features for a prediction rule in accordance with an embodiment of the present invention. At stage 102, a prediction rule (e.g., a linear prediction rule, of the form shown in equation (1)) may be generated based on data for a cohort of one or more instances (e.g., patients), where each instance may include measurements of n feature(s) and an outcome with respect to the event, to the extent the outcome is known. As described above, generating a linear prediction rule involves determining weights of the n features in the rule. The datasets may include non-censored and/or right-censored data, and the prediction rule may be generated by, for example, SVRc described in above-referenced, commonly-owned U.S. patent application Ser. No. 10/991,240 (U.S. Pub. No. 20050108753), which is hereby incorporated by reference herein in its entirety. The n feature(s) may be selected based on domain expertise and/or another feature selection procedure. In the medical context, for example, the n features may include one or more clinical features, one or more molecular features, and/or one or more computer-generated tissue image ("morphometric") features. Examples of features that may correlate with prostate cancer (and other medical conditions) are described in above-incorporated U.S. patent application Ser. No. 10/991,240, as well as commonly-owned U.S. patent application Ser. No. 11/080,360, filed Mar. 14, 2005 (U.S. Pub. No. 20050262031), and Ser. No. 11/200,758, filed Aug. 9, 2005, both of which are hereby incorporated by reference herein in their entireties. In a preferred embodiment, no pre-filtering of the n features is performed (e.g., but can be performed optionally in other embodiments), which pre-filtering may involve requiring each of the n features to produce a minimum value of the concordance index (CI) (or other statistical metric) when taken alone in order for that feature to be included in the set of n features.

At stage 104, a value of rule fitness may be determined for the prediction rule by, for example, evaluating feature data for a cohort of one or more instances with the prediction rule and comparing the outcomes produced by the prediction rule to known outcomes for the subjects through the use of a statistical metric. In a preferred embodiment, the cohort of instances evaluated by the prediction rule at stage 104 is the same cohort of instances used to generate the rule (minus the outcomes to the extent known). In an embodiment, the following metric may be used to determine the fitness of the prediction rule:

$$\text{Prediction rule fitness} = \text{concordance index(CI)} + \text{sensitivity}*\text{specificity} \quad (4)$$

The CI may be determined for censored and/or non-censored data using the procedure described in above-incorporated, commonly-owned U.S. application Ser. No. 11/080,360, as well as commonly-owned U.S. application Ser. No. 11/067,066, filed Feb. 25, 2005 (U.S. Pub. No. 20050197982), which is hereby incorporated by reference herein in its entirety. The sensitivity and specificity may be determined for prediction rules with continuous output according to the procedure set forth in FIG. 2. For prediction rules with binary output, sensitivity and specificity may be determined using procedures known in the art. As described in connection with FIGS. 3 and 4, the metric in (4) has achieved promising results with respect to feature selection.

Thus, stage 104 may involve the substages of determining a value of the CI of the prediction rule, determining a value of the sensitivity of the prediction rule, determining a value of the specificity of the prediction rule, and using these values to determine the fitness of the rule according to (4). Generally, sensitivity measures the ability of a rule to predict an outcome when it is truly present. In the medical context, sensitivity may be calculated as the proportion of all patients having a medical condition who are correctly classified as such by the prediction rule, which can be determined as the number of true positives divided by the sum of true positives+false negatives. Specificity, on the other hand, measures the ability of the prediction rule to exclude the presence of an outcome when it is truly not present. For example, specificity may be calculated as the proportion of patients who do not have a medical condition that are correctly classified as such by the prediction rule, which can be expressed as the number of true negatives divided by the sum of true negatives+false positives. The CI measures the proportion of subject pairs in which the subject with the higher actual response also has the higher predicted response. For example, in the context of predicting cancer recurrence, the CI represents the proportion of times that the patient predicted to recur earlier by the prediction rule actually does recur earlier. The CI typically ranges from 0 to 1.0 (perfect predictive ability). A predictive ability of 0.5 signals that a prediction rule is no more reliable than a coin toss.

In other embodiments, other metric(s) of prediction rule fitness may be used in accordance with the present invention. For example, the metric of prediction rule fitness may be the concordance index or some other statistic characterizing the correlation between the prediction rule's output and the known outcomes of the training instances. As another example, a measure of separation between the predicted outcome value(s) and actual outcome(s) may be used as a fitness metric (e.g., the average absolute difference between the predicted and actual target values). Still another example, any of the sensitivity, specificity, accuracy, and positive and/or negative predicted values of the prediction rule can be used as a metric of prediction rule fitness (e.g., for binary or binarized outcomes). As another example, prediction rule fitness may be determined based on the following risk functional: R(k, L)=fitness/(1−sqrt((k(log(L/k)+1)+log(L)/2)/L)), where L is number of instances in the dataset, k is a VC-dimension of the set of functions from which the prediction rule is chosen, and fitness is a function that evaluates quality of fit of the prediction rule.

At stage 106, a contribution to the prediction rule may be determined for each of the n features in the rule. For example, the following statistical metric may be used to determine the contribution of each feature:

$$\text{Contribution } f_i = w_i * g(\text{variance}_i) \quad (5)$$

where $w_i$ is the weight of feature $f_i$ within the prediction rule and g is a monotone function of $\text{variance}_i$ that measures the discriminative ability of feature $f_i$ as observed in the data used to generate the rule. For example, in one embodiment, g(variance$_i$) may be the variance of feature $f_i$. In another embodiment, g(variance$_i$) may be the standard deviation of feature $f_i$, which is the square route of the variance of feature $f_i$. Variance$_i$ is calculated by summing the squares of the deviations of the values for feature $f_i$ observed in the data used to generate the prediction rule (i.e., the deviation for a given value being the difference between that value and the mean of all values for the feature $f_i$) and then dividing this sum by the number of values. For example, when the five values 1, 4, 9, 11, and 15 for a feature are observed in the data used to generate the prediction rule (e.g., when data for five instances is used to generate the rule), the mean for that feature is 8 (i.e., 40/5) and the variance of that feature is $((1-8)^2+(4-8)^2+(9-8)^2+(11-8)^2+(15-8)^2)/5=24.8$. In contrast to the criterion shown in (2) and (3) (which is used with LSR (Least Squares Regression) and not SVM or SVRc), the metric in (5) does not consider the error of the regression (which consideration limits the use of the metric in (2) and (3) to models generated based on non-censored data only).

In other embodiments, other metric(s) of feature contribution may be used in accordance with the present invention. For example, the weight of a feature in a linear predictive model can be used as a measure of the feature contribution. As another example, the variance of a feature can be used as a measure of the feature contribution. Still another example, statistic(s) characterizing the correlation between feature and outcome can be used as a measure of feature contribution. As another example, the metric of feature contribution can be the weight of a feature multiplied by the concordance index for that feature.

At stage 108, the feature having the lowest contribution to the prediction rule is removed from consideration, in order to reduce the feature set to n−1 features. For example, this may involve evaluating all of the features in the prediction rule according to the absolute value of their contribution to the rule and removing the feature having the lowest contribution from the feature set. This is in contrast to the greedy backward procedure that determines which feature from a current prediction rule to remove from consideration by generating and evaluating the predictive abilities of n new (n−1)-feature prediction rules (each new rule leaving out a respective one of the features in the current prediction rule). Thus, this difference produces a reduction in the processing resources (e.g., number of models that must be generated) needed to implement procedure 100. Another difference is that the greedy backward procedure stops removing features in the current model from consideration when none of the new (n−1)-feature prediction rules has the same or a higher predictive ability than the current rule, whereas procedure 100 continues to remove features from the feature set without regard to the predictive ability of the (n−1)-feature prediction rule. This allows procedure 100 to determine whether the removal of 2 or more features causes an overall increase in predictive ability, even when the removal of a first feature (i.e., the feature with the lowest contribution value) causes a decrease in predictive ability. Notably, the present inventors have determined that the predictive ability of a prediction rule often does not decrease monotonically with the removal of each feature.

Subsequent to stage 108, procedure 100 returns to stage 102 at which a prediction rule is generated based on data for the reduced set of n−1 features, as well as outcomes, to the extent the outcomes are known. For example, the same data that was used to the generate the n-feature rule may be used to generate the (n−1)-feature prediction rule, with the exception that the data used to generate the (n−1)-feature rule excludes the data for the feature removed from consideration at stage 108. Successive iterations of stages 102-108 may be performed until all but one feature has been removed from the feature set. For example, at stage 110 (e.g., immediately following stage 104 of determining rule fitness), it may be determined whether the current set of features includes more than one feature. If the answer is in the affirmative, the procedure may proceed to stage 106 described above. If the answer is in the negative, the procedure may proceed to stage 112 at which the final prediction rule is selected to be the rule that has the highest value of fitness measured in stage 104. In the case of multiple prediction rules with equivalent fitness values, the prediction rule with the fewest number of features can be selected.

Thus, whereas procedure 100 can involve the generation of n prediction rules in order to select the set of features for the final predictive model, namely one n-feature prediction rule, one (n−1)-feature prediction rule, one (n−2)-feature prediction rule, . . . , and one 1-feature prediction rule, this number of rules is reduced significantly in comparison to, for example, the number of prediction rules generated according to the greedy forward procedure. For example, starting with a set of n=500 features, procedure 100 can involve the generation of 500 prediction rules in order to select the final set of features, as compared to the potentially as many as 125,250 prediction rules generated according to the greedy forward procedure.

Figure 2:
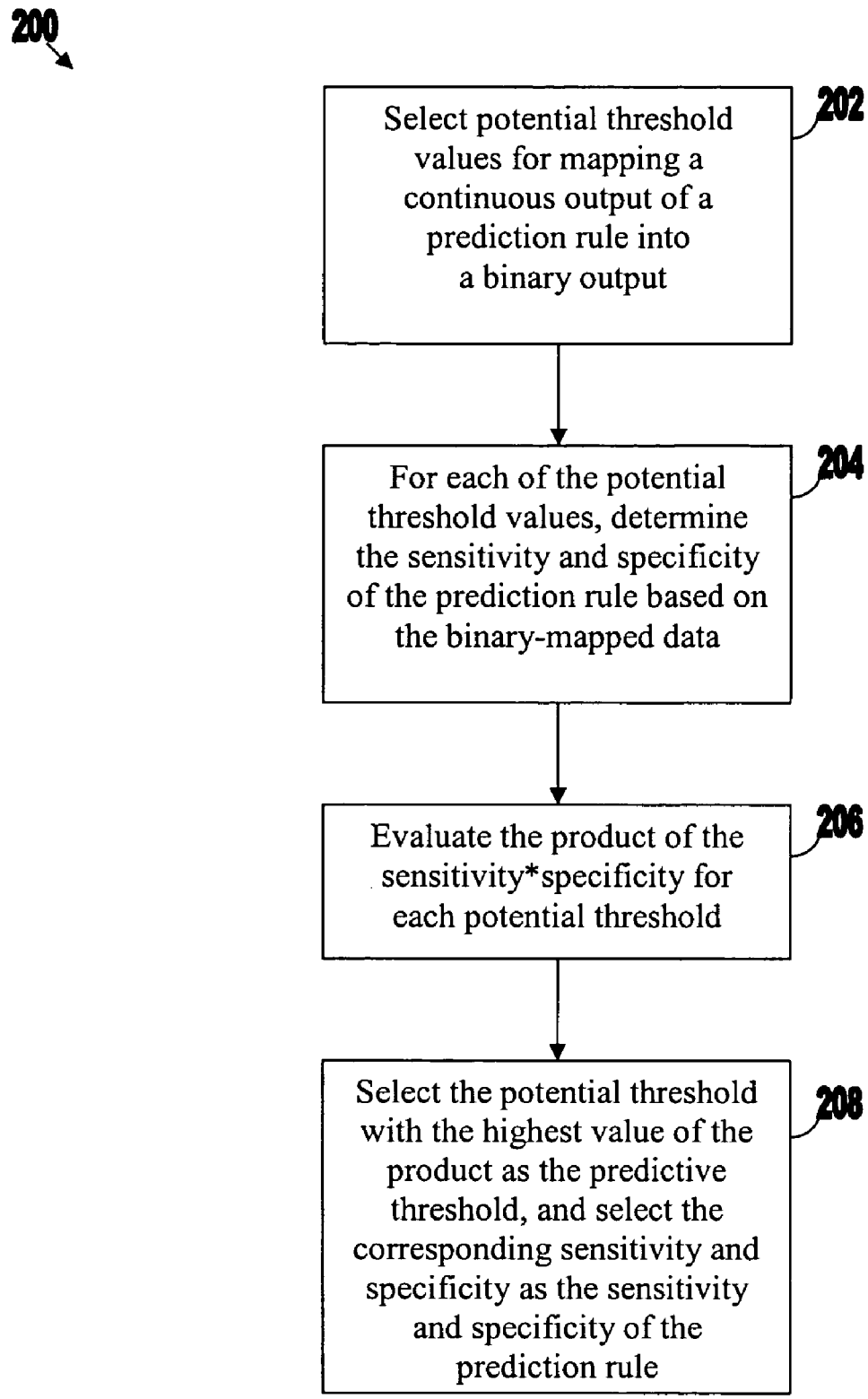
FIG. 2 is a flowchart of illustrative stages involved in determining the sensitivity and specificity of a prediction rule with a continuous output in accordance with an embodiment of the present invention.

FIG. 2 is a flowchart 200 of illustrative stages involved in stage 104 (FIG. 1) of determining the fitness of a prediction rule. More particularly, flowchart 200 illustrates a method for determining the sensitivity and specificity of a prediction rule having a continuous output (e.g., a regression model). Generally, the method involves mapping the continuous output into a binary output for evaluation. For example, if the prediction rule outputs a value representative of a predicted time to an event, a threshold may be provided that separates early events from late events. At stage 102, potential threshold values are selected for mapping the rule output into a binary output. Particularly, every value of the output of the prediction rule on the training data is taken one after another as a potential threshold for the prediction. At stage 204, for each of the potential thresholds, the sensitivity and specificity of the prediction rule is determined based on the binary-mapped data. To the extent that censored data was used to generate the prediction rule, the censored data for instances with actual outcomes that are below the potential threshold are not included in the calculation of sensitivity and specificity. For example, if the potential threshold represents a time to event of 3 months, data is not included for censored instances (i.e., instances that have yet to experience the event) that have observation times less than 3 months. At stage 206, each potential threshold is evaluated by the product of sensitivity and specificity calculated for the potential threshold. At stage 208, the potential threshold with the highest value of the product is selected as the predictive threshold, and its sensitivity and specificity are considered to be the sensitivity and specificity of the prediction rule.

Prostate Cancer Recurrence Examples

A series of experiments were conducted to generate prediction rules that predicted time to recurrence of prostate cancer (PSA recurrence) in patients who had undergone radical prostatectomy. These experiments compared final prediction rules generated according to the feature selection procedure of FIG. 1 to prediction rules generated without the procedure. More specifically, final prediction rules were generated without the use of feature selection procedure 100 (FIG. 1) by applying SVRc to feature data and associated patient outcomes (to the extent known) for a cohort of instances. Final prediction rules were also generated based on the same feature and outcome data for the instances, but by subjecting the data to feature selection procedure 100.

In a first experiment, a 262 patient cohort (cohort 1) was used to generate and evaluate the prediction rules. In a second experiment, a 154 patient cohort (cohort 2) was combined with cohort 1 for a complete 416 record, 287 patient cohort (cohort 1+2) that was used to generate the prediction rules. The differences in cohort 1 and cohort 2 were in the morphometric features in that images in cohort 2 were of tissues from tissue microarrays (TMAs), whereas images in cohort 1 were of full tissue cross-sections. In the first and second experiments, the final prediction rules were validated based on a cohort consisting of 82 cores from 61 unique patients (cohort 3). In both experiments, patients who had received neoadjuvant or adjuvant hormonal (or radiation) therapy were considered non-evaluable and were not included.

For each of the first and second experiments, three sub-experiments were performed. The first sub-experiment generated prediction rules based on clinical and molecular (AR-IHC) features (and outcomes to the extent the outcomes were known). The second sub-experiment generated prediction rules based on clinical, molecular (AR-IHC), and morphometric features, and outcomes to the extent known, where the morphometric features were generated by the Magic™ script v5.0 proprietary software and included measurements of the following histopathological objects: cytoplasm, epithelial nuclei, stroma, and lumen. The third sub-experiment generated prediction rules based on clinical, molecular (AR-IHC) and morphometric features, and outcomes to the extent known, where the morphometric features were taken by the Magic™ software and measured the degree of nucleic density in images and level of nuclei in stroma. A more detailed description of these features (and of the Magic™ software for generating the morphometric features) is provided in above-incorporated, commonly-owned U.S. patent application Ser. No. 11/080,360.

FIGS. 3 and 4 are tables that include the results of these experiments. As shown, the use of procedure 100 resulted in simplified prediction rules in every instance, meaning that every final prediction rule generated through the use of procedure 100 had a reduced number of features in comparison to the corresponding prediction rule generated without the use of procedure 100. Advantageously, a reduced number of features conserves the resources of physicians, other individuals, and/or automated processing equipment (e.g., a tissue image analysis system running the Magic™ software) involved in measuring the features in new patients who are to be evaluated by the final model. Additionally, in every instance, the final prediction rule generated by procedure 100 had about the same or better predictive ability than the corresponding prediction rule generated without procedure 100.

FIG. 3 shows the results of experiment 1. In sub-experiment 1, the final prediction rule generated according to procedure 100 included 6 features and had a validation fitness value of 1.23 (i.e., see equation (4), where validation CI=0.75, validation sensitivity=0.79, validation specificity=0.61), whereas the final prediction rule generated without procedure 100 included 10 features and had a validation fitness value of 1.24 (i.e., validation CI=0.76, validation sensitivity=0.79, validation specificity=0.61). The validation values are the values of the CI, sensitivity, and specificity obtained by evaluating the prediction rules with data independent from the data used to generate the rules. In the second sub-experiment, the final prediction rule generated according to procedure 100 included 6 features and had a validation fitness value of 1.43 (i.e., validation CI=0.8, validation sensitivity=0.91, validation specificity=0.7), whereas the final prediction rule generated without procedure 100 included 43 features and had a validation fitness value of 1.45 (i.e., validation CI=0.81, validation sensitivity=0.91, validation specificity=0.7). In the third sub-experiment, the final prediction rule generated according to procedure 100 included 10 features and had a validation fitness value of 1.41 (i.e., validation CI=0.8, validation sensitivity=0.85, validation specificity=0.73), whereas the final prediction rule generated without procedure 100 included 14 features and had a validation fitness value of 1.42 (i.e., validation CI=0.8, validation sensitivity=0.85, validation specificity=0.73). FIG. 2 also shows the training CI, sensitivity, specificity and fitness values of the final prediction rules generated in experiment I (i.e., the values of CI, sensitivity, and specificity obtained by evaluating the models with the same data used to generate the rules).

FIG. 4 shows the results of experiment 2. In sub-experiment 1, the final prediction rule generated according to procedure 100 included 6 features and had a validation fitness value of 1.23 (i.e., validation CI=0.75, validation sensitivity=0.79, validation specificity=0.61), whereas the final prediction rule generated without procedure 100 included 10 features and had a validation fitness value of 1.24 (i.e., validation CI=0.75, validation sensitivity=0.79, validation specificity=0.61). In the second sub-experiment, the final prediction rule generated according to procedure 100 included 13 features and had a validation fitness value of 1.38 (i.e., validation CI=0.81, validation sensitivity=0.85, validation specificity=0.67), whereas the final prediction rule generated without procedure 100 included 43 features and had a validation fitness value of 1.4 (i.e., validation CI=0.81, validation sensitivity=0.88, validation specificity=0.67). In the third sub-experiment, the final prediction rule generated according to procedure 100 included 8 features and had a validation fitness value of 1.36 (i.e., validation CI=0.81, validation sensitivity=0.91, validation specificity=0.61), whereas the final prediction rule generated without procedure 100 included 14 features and had a validation fitness value of 1.34 (i.e., validation CI=0.8, validation sensitivity=0.82, validation specificity=0.67). FIG. 3 also shows the training CI, sensitivity, specificity and fitness values of the final prediction rules generated in experiment 2.

FIG. 5 is a table that shows the model weight and contribution value for each of the 14 features eligible for inclusion in the final prediction rule generated according to procedure 100 in sub-experiment 2 of experiment 1 (FIG. 2), subsequent to a first iteration of stages 102 and 106. As shown, the morphometric feature "RelAreaOfHighNucleiDensity" has the lowest absolute value of contribution (as determined according to equation (5)) at 0.16444. Thus, this feature would be removed from the feature set at stage 108 in order to produce a reduced set of 13 features. The abbreviations of the 10 clinical and molecular features in FIG. 5 are shown below in unabbreviated form. The 4 morphometric features shown in FIG. 5 (RelAreaOfLowNucleiDensity, RelAreaOfMediumNucleiDensity, RelAreaOfHighNucleiDensity, and AreaOfNucleiInStromaPx10363) are named according to a naming convention described in above-incorporated, commonly-owned U.S. patent application Ser. No. 11/080,360.

| Clinical Features: | |
|---|---|
| bxggl | Dominant biopsy Gleason score |
| Bxggtot | Biopsy Gleason grade |
| Prepsa | Preoperative PSA (prostate-specific antigen) |
| Ln | Lymph node status |
| Margins | Surgical margin status |
| Ece | Extracapsular Invasion |
| Svi | Seminal vesicle invasion |
| ggl | Dominant prostatectomy Gleason score |
| ggtot | Prostatectomy Gleason grade |
| Molecular Feature: | |
| Arsi | Androgen Receptor (AR) tumor staining index |

Thus it is seen that systems and methods are provided for selecting features for a final prediction rule, which rule may be embodied as a computer-implemented model. Although particular embodiments have been disclosed herein in detail, this has been done by way of example for purposes of illustration only, and is not intended to be limiting with respect to the scope of the appended claims, which follow. Any lettering (e.g., (a), (b), (c), etc.) in the following claims is used for reference purposes only, and is not meant to require the claim elements to be performed in any specific order. For example, stage (b) could be performed before stage (a), and so on. It is contemplated by the inventors that various substitutions, alterations, and modifications may be made without departing from the spirit and scope of the invention as defined by the claims. Other aspects, advantages, and modifications are considered to be within the scope of the following claims. The claims presented are representative of the inventions disclosed herein. Other, unclaimed inventions are also contemplated. The inventors reserve the right to pursue such inventions in later claims.

For example, one or more (e.g., all) of stages 102-112 may be implemented at least in part using a computer system, which may include hardware, software, or any suitable combination thereof. Thus, it will be appreciated that a computer program for implementing at least part of procedure 100 is envisaged as an aspect of the present invention. The computer system may be any suitable apparatus, system or device. For example, the computer system may be a programmable data processing apparatus, a general purpose computer, a Digital Signal Processor or a microprocessor. The computer program may be embodied as source code and undergo compilation for implementation on a computer, or may be embodied as object code, for example.

It is also conceivable that some or all of the functionality ascribed to the computer program or computer system aforementioned may be implemented in hardware, for example by means of one or more application specific integrated circuits.

Suitably, the computer program can be stored on a carrier medium in computer usable form, which is also envisaged as an aspect of the present invention. For example, the carrier medium may be a computer readable medium such as solid-state memory, optical or magneto-optical memory such as a readable and/or writable disk for example a compact disk (CD) or a digital versatile disk (DVD), or magnetic memory such as disc or tape, and the computer system can utilize the program to configure it for operation. The computer program may also be supplied from a remote source embodied in a carrier medium such as an electronic signal, including a radio frequency carrier wave or an optical carrier wave.

What is claimed is:

1. A method for selecting features for a final prediction rule predictive of an outcome with respect to a medical condition, said method comprising:

performing with a computer-implemented machine learning tool:

(a) generating a prediction rule based on training data for a cohort of patients whose outcomes with respect to said medical condition are at least partially known, wherein for each patient the data comprises measurements for a set of features and the outcome with respect to said medical condition for said patient to the extent known, wherein in a first iteration of (a) said set of features includes n features with n greater than or equal to 3 with n being decremented by one in each subsequent iteration of (a);

(b) determining a fitness value for said prediction rule, wherein said determining a fitness value comprises summing a concordance index (CI) of said prediction rule with a product of a sensitivity and a specificity of said prediction rule;

(c) determining a value of contribution to said prediction rule for each of said features in said set of features;

(d) removing a feature from consideration from said set of features based on the values of contribution, wherein the feature having the lowest value of contribution is removed;

(e) iterating (a)-(d) in order to produce n prediction rules and n fitness values; and (f) selecting, based on the fitness values for said n prediction rules, one of said n prediction rules as said final prediction rule predictive of the outcome with respect to said medical condition, wherein of said n prediction rules said final prediction rule has the highest predictive ability with respect to the outcome with respect to said medical condition as indicated by said fitness values; and evaluating data for a patient with a computer implementation of said final prediction rule to produce a value predictive of the patient's outcome with respect to said medical condition.

2. The method of claim 1, wherein stages (a)-(f) are performed in that order.

3. The method of claim 1, wherein said determining a value of contribution comprises determining a contribution value for each feature i by multiplying a weight of said feature i in said prediction rule with a measure of the discriminative ability of said feature i as observed in the data used to generate said prediction rule.

4. The method of claim 1, wherein said determining a value of contribution comprises determining a contribution value for each feature i by multiplying a weight of said feature i in said prediction rule with a concordance index (CI) for said feature i.

5. The method of claim 1, wherein said iterating (a)-(d) comprises:

repeating (a) and (b) as long as said set of features includes 1 or more features; and repeating (c) and (d) as long as said set of features includes 2 or more features.

6. The method of claim 1, wherein said generating a prediction rule comprises generating a prediction rule based on support vector regression for censored data with a linear kernel.

7. The method of claim 1, wherein said determining a value of contribution comprises determining a contribution value for each feature by multiplying a weight of said feature in said prediction rule with a variance or standard deviation of said measurements of said feature as observed in the training data used to generate said prediction rule.

8. A method for selecting features for a final prediction rule predictive of an outcome with respect to a medical condition, said method comprising:

performing with a computer-implemented machine learning tool:

(a) generating a prediction rule based on training data for a cohort of patients whose outcomes with respect to said medical condition are at least partially known, wherein for each patient the data comprises measurements for a set of features and the outcome with respect to said medical condition for said patient to the extent known, wherein in a first iteration of (a) said set of features includes n features with n greater than or equal to 3 with n being decremented by one in each subsequent iteration of (a);

(b) determining a fitness value for said prediction rule, wherein said determining a fitness value comprises calculating the following risk functional:

$$R(k, L) = \text{fitness}/(1-\text{sqrt}(\,(k\,(\log(L/k)+\log(L)/2)/L))$$

where L is a number of instances in said data for said set of n features, k is a VC-dimension of a set of functions from which said prediction rule is selected, and fitness is a function that evaluates quality of fit of said prediction rule;

(c) determining a value of contribution to said prediction rule for each of said features in said set of features;

(d) removing a feature from consideration from said set of features based on the values of contribution, wherein the feature having the lowest value of contribution is removed;

(e) iterating (a)-(d) in order to produce n prediction rules and n fitness values; and (f) selecting, based on the fitness values for said n prediction rules, one of said n prediction rules as said final prediction rule predictive of the outcome with respect to said medical condition, wherein of said n prediction rules said final prediction rule has the highest predictive ability with respect to the outcome with respect to said medical condition as indicated by said fitness values; and evaluating data for a patient with a computer implementation of said final prediction rule to produce a value predictive of the patient's outcome with respect to said medical condition.

9. The method of claim 8, wherein said generating a prediction rule comprises generating a prediction rule based on support vector regression for censored data with a linear kernel.

10. The method of claim 8, wherein said determining a value of contribution comprises determining a contribution value for each feature by multiplying a weight of said feature in said prediction rule with a variance or standard deviation of said measurements of said feature as observed in the training data used to generate said prediction rule.

11. An apparatus for determining a risk of occurrence of an outcome with respect to a medical condition in a patient, said apparatus comprising:

a computer implementation of a final prediction rule predictive of said medical condition, wherein said final prediction rule is based on features selected through machine learning, said machine learning comprising performing with a computer-implemented machine learning tool (a) generating a prediction rule based on training data for a cohort of patients whose outcomes with respect to said medical condition are at least partially known, wherein for each patient the data comprises measurements for a set of features and the outcome with respect to said medical condition for said patient to the extent known, wherein in a first iteration of (a) said set includes n features with n greater than or equal to 3 with n being decremented by one in each subsequent iteration of (a), (b) determining a fitness value for said prediction rule, wherein said determining a fitness value comprises summing a concordance index (CI) of said prediction rule with a product of a sensitivity and a specificity of said prediction rule, (c) determining a value of contribution to said prediction rule for each of said features in said set of features, (d) removing a feature from consideration from said set of features based on the values of contribution, wherein the feature having the lowest value of contribution is removed, (e) iterating (a)-(d) in order to produce n prediction rules and n fitness values, and (f) selecting, based on the fitness values for said n prediction rules, one of said n prediction rules as said final prediction rule, wherein of said n prediction rules said final prediction rule has the highest predictive ability with respect to the outcome with respect to said medical condition as indicated by said fitness values, wherein said computer implementation of said final prediction rule:

receives data for said patient; and evaluates said data for said patient according to said final prediction rule, thereby determining a value predictive of the patient's outcome with respect to said medical condition.

12. The apparatus of claim 11, wherein said machine learning determines a value of contribution for each feature i by multiplying a weight of said feature i in said prediction rule with a measure of the discriminative ability of said feature i as observed in the data used to generate said prediction rule.

13. The apparatus of claim 11, wherein said machine learning determines a value of contribution for each feature i by multiplying a weight of said feature i in said prediction rule with a concordance index (CI) for said feature i.

14. The apparatus of claim 11, wherein said generating a prediction rule comprises generating a prediction rule based on support vector regression for censored data with a linear kernel.

15. The apparatus of claim 11, wherein said determining a value of contribution comprises determining a contribution value for each feature by multiplying a weight of said feature in said prediction rule with a variance or standard deviation of said measurements of said feature as observed in the training data used to generate said prediction rule.

16. An apparatus for determining a risk of occurrence of an outcome with respect to a medical condition in a patient, said apparatus comprising:

a computer implementation of a final prediction rule predictive of said medical condition, wherein said final prediction rule is based on features selected through machine learning, said machine learning comprising performing with a computer-implemented machine learning tool (a) generating a prediction rule based on training data for a cohort of patients whose outcomes with respect to said medical condition are at least partially known, wherein for each patient the data comprises measurements for a set of features and the outcome with respect to said medical condition for said patient to the extent known, wherein in a first iteration of (a) said set includes n features with n greater than or equal to 3 with n being decremented by one in each subsequent iteration of (a), (b) determining a fitness value for said prediction rule, wherein said determining a fitness value comprises calculating the following risk functional:

$$R(k, L) = \text{fitness}/(1-\text{sqrt}((k\,(\log(L/k)+\log(L)+\log(L)/2)/L))$$

where L is a number of instances in said data for said set of n features, k is a VC-dimension of a set of functions from which said prediction rule is selected, and fitness is a function that evaluates quality of fit of said prediction rule, (c) determining a value of contribution to said prediction rule for each of said features in said set of features, (d) removing a feature from consideration from said set of features based on the values of contribution, wherein the feature having the lowest value of contribution is removed, (e) iterating (a)-(d) in order to produce n prediction rules and n fitness values, and (f) selecting, based on the fitness values for said n-prediction rules, one of said n prediction rules as said final prediction rule, wherein of said n prediction rules said final prediction rule has the highest predictive ability with respect to the outcome with respect to said medical condition as indicated by said fitness values, wherein said computer implementation of said final prediction rule:

receives data for said patient; and evaluates said data for said patient according to said final prediction rule, thereby determining a value predictive of the patient's outcome with respect to said medical condition.

17. The apparatus of claim 16, wherein said generating a prediction rule comprises generating a prediction rule based on support vector regression for censored data with a linear kernel.

18. The apparatus of claim 16, wherein said determining a value of contribution comprises determining a contribution value for each feature by multiplying a weight of said feature in said prediction rule with a variance or standard deviation of said measurements of said feature as observed in the training data used to generate said prediction rule.

19. A computer readable medium comprising computer executable instructions recorded thereon for performing a method for selecting features for a final prediction rule predictive of an outcome with respect to a medical condition, the method comprising:

performing with a computer-implemented machine learning tool:

(a) generating a prediction rule based on training data for a cohort of patients whose outcomes with respect to said medical condition are at least partially known, wherein for each patient the data comprises measurements for a set of features and the outcome with respect to said medical condition for said patient to the extent known, wherein in a first iteration of (a) said set includes n features with n greater than or equal to 3 with n being decremented by one in each subsequent iteration of (a);

(b) determining a fitness value for said prediction rule, wherein said determining a fitness value comprises summing a concordance index (CI) of said prediction rule with a product of a sensitivity and a specificity of said prediction rule;

(c) determining a value of contribution to said prediction rule for each of said features in said set of features;

(d) removing a feature from consideration from said set of features based on the values of contribution, wherein the feature having the lowest value of contribution is removed;

(e) iterating (a)-(d) to produce n prediction rules and n fitness values;

(f) selecting, based on the fitness values for said n prediction rules, one of said n prediction rules as the basis for said final prediction rule predictive of the outcome with respect to said medical condition, wherein of said n prediction rules said final prediction rule has the highest predictive ability with respect to the outcome with respect to said medical condition as indicated by said fitness values; and evaluating data for a patient with a computer implementation of said final prediction rule to produce a value predictive of the patient's outcome with respect to said medical condition.

20. The computer readable medium of claim 19, further comprising computer executable instructions recorded thereon for determining a value of contribution by performing the method comprising determining a contribution value for each feature i by multiplying a weight of said feature i in said prediction rule with a measure of the discriminative ability of said feature i as observed in the data used to generate said prediction rule.

21. The computer readable medium of claim 19, further comprising computer executable instructions recorded thereon for determining a value of contribution by performing the method comprising determining a contribution value for each feature i by multiplying a weight of said feature i in said prediction rule with a concordance index (CI) for said feature i.

22. The computer readable medium of claim 19, wherein said generating a prediction rule comprises generating a prediction rule based on support vector regression for censored data with a linear kernel.

23. The computer readable medium of claim 19, wherein said determining a value of contribution comprises determining a contribution value for each feature by multiplying a weight of said feature in said prediction rule with a variance or standard deviation of said measurements of said feature as observed in the training data used to generate said prediction rule.

24. A computer readable medium comprising computer executable instructions recorded thereon for performing a method for selecting features for a final prediction rule predictive of an outcome with respect to a medical condition, the method comprising:

performing with a computer-implemented machine learning tool:

(a) generating a prediction rule based on training data for a cohort of patients whose outcomes with respect to said medical condition are at least partially known, wherein for each patient the data comprises measurements for a set of features and the outcome with respect to said medical condition for said patient to the extent known, wherein in a first iteration of (a) said set includes n features with n greater than or equal to 3 with n being decremented by one in each subsequent iteration of (a);

(b) determining a fitness value for said prediction rule, wherein said determining a fitness value comprises calculating the following risk functional:

$R(k, L) = \text{fitness}/(1-\text{sqrt}(\,(k\,(\log(L/k)+\log(L)/2)/L))$ where L is a number of instances in said data for said set of n features, k is a VC-dimension of a set of functions from which said prediction rule is selected, and fitness is a function that evaluates quality of fit of said prediction rule;

(c) determining a value of contribution to said prediction rule for each of said features in said set of features;

(d) removing a feature from consideration from said set of features based on the values of contribution, wherein the feature having the lowest value of contribution is removed;

(e) iterating (a)-(d) to produce n prediction rules and n fitness values;

(f) selecting, based on the fitness values for said n prediction rules, one of said n prediction rules as the basis for said final prediction rule predictive of the outcome with respect to said medical condition, wherein of said n prediction rules said final prediction rule has the highest predictive ability with respect to the outcome with respect to said medical condition as indicated by said fitness values; and evaluating data for a patient with a computer implementation of said final prediction rule to produce a value predictive of the patient's outcome with respect to said medical condition.

25. The computer readable medium of claim 24, wherein said generating a prediction rule comprises generating a prediction rule based on support vector regression for censored data with a linear kernel.

26. The computer readable medium of claim 24, wherein said determining a value of contribution comprises determining a contribution value for each feature by multiplying a weight of said feature in said prediction rule with a variance or standard deviation of said measurements of said feature as observed in the training data used to generate said prediction rule.

* * * * *